United States Patent [19]

Kim

[11] Patent Number: 4,792,735
[45] Date of Patent: Dec. 20, 1988

[54] APPARATUS FOR ADJUSTING TORQUE AND SPEED OF A DENTIST HANDPIECE D.C. MOTOR

[76] Inventor: In-Suk Kim, Samik Apt 10-615 Chungdam-dong 134-21, Gangnam-gu, Seoul, Rep. of Korea

[21] Appl. No.: 69,291

[22] Filed: Jul. 2, 1987

[51] Int. Cl.$^4$ .............................. G05B 5/00
[52] U.S. Cl. ................... 318/317; 318/308; 318/332; 361/57
[58] Field of Search ............ 318/308, 309, 310–317, 318/332, 333, 345; 361/18, 57

[56] References Cited

U.S. PATENT DOCUMENTS

| | | | |
|---|---|---|---|
| 3,359,434 | 12/1967 | Galluzzi | 361/57 |
| 3,396,323 | 8/1968 | Auld | 318/331 |
| 3,725,739 | 4/1973 | Gniffey | 361/57 |
| 4,384,241 | 5/1983 | Stillhard | 318/331 |
| 4,494,057 | 1/1985 | Hotta | 318/317 |
| 4,594,633 | 6/1986 | Townsend et al. | 361/57 |

Primary Examiner—William M. Shoop, Jr.
Assistant Examiner—David Martin
Attorney, Agent, or Firm—Richard C. Woodbridge

[57] ABSTRACT

A D.C. motor control circuit for a dentist's hand drill including a feedback loop to vary the torque of the motor according to the load on the motor while keeping the motor speed constant. Power to the motor is provided through a three terminal regulating IC circuit. The IC regulating circuit is protected against power surges by an overload detecting circuit incorporated into the feedback loop.

1 Claim, 2 Drawing Sheets

4,792,735

APPARATUS FOR ADJUSTING TORQUE AND SPEED OF A DENTIST HANDPIECE D.C. MOTOR

BACKGROUND OF THE INVENTION

1. Field of the Invention

The present invention relates to an apparatus for adjusting the torque of a D.C. motor running at constant speed.

2. Background of Related Art

The speed of a conventional dentist's hand drill motor is manually adjusted by adjusting the amount of electrical current controlled by a foot pedal regulator which varies the amount of resistance in the circuit. Under such circumstances the torque of the motor is variable and when the load on the motor increases, the speed of the motor decreases and finally stops.

SUMMARY OF THE INVENTION

Briefly described, the present invention comprises a motor for a dentist's hand drill which can operate at constant torque at any given speed of the motor. A three terminal regulator consisting of an integrated circuit IC chip, controls current from a D.C. source to the motor. A feedback loop provides a signal to an R.C. circuit connected to the common input of the three terminal regulator. The circuit further includes a surge protecting safety circuit for preventing overloads on the common input terminal of the IC.

The invention can be more fully understood by reference to the following drawings.

DETAILED DESCRIPTION OF THE INVENTION

The same numbers will be used to refer to the same element as found in the figures which illustrate the invention.

Figure 1:
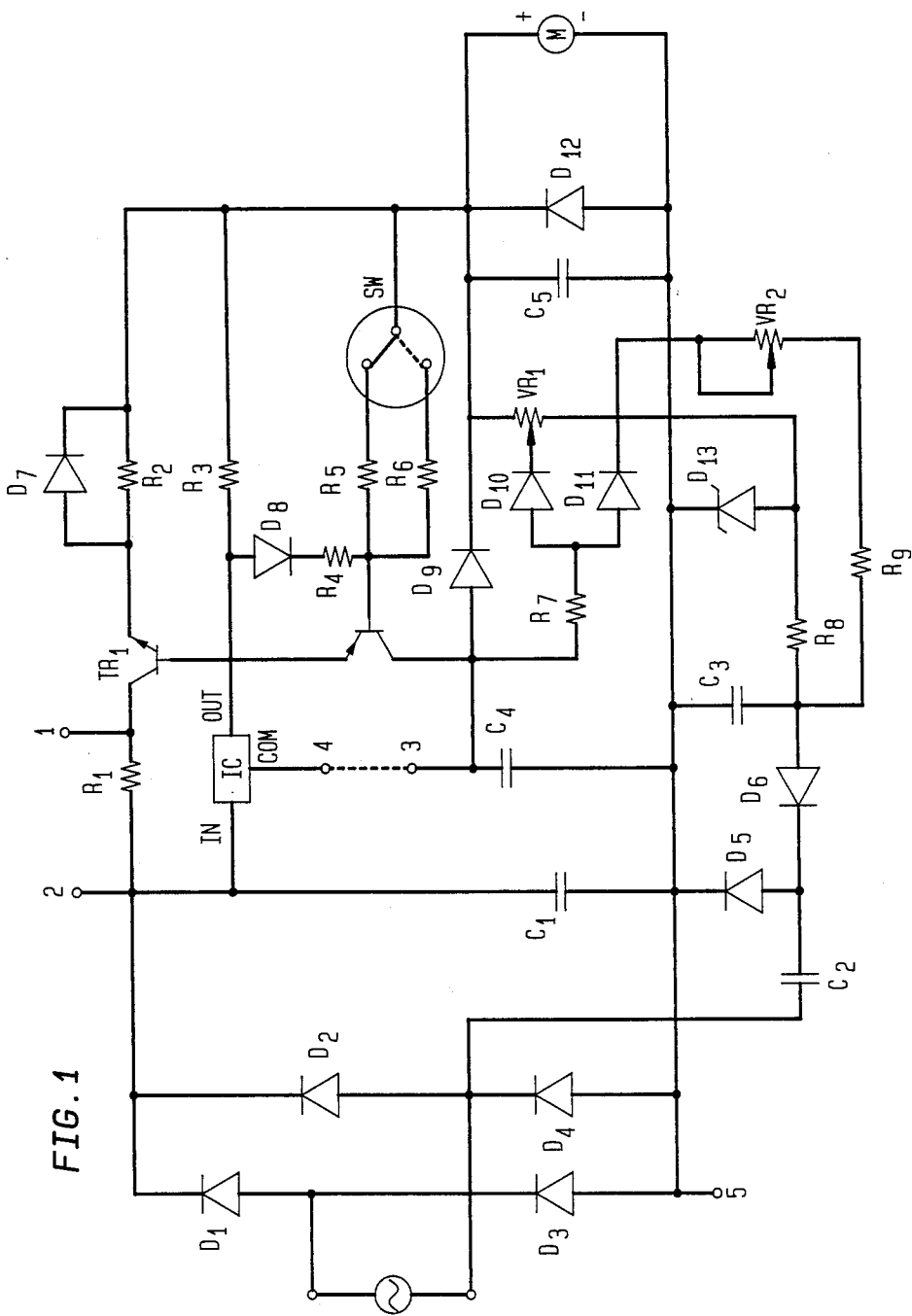
FIG. 1 is a circuit diagram of the preferred embodiment of the present invention.

In FIG. 1, electrical current from the A.C. electrical source 2 is rectified by a diode bridge, including diodes $D_1, D_2, D_3$ and $D_4$, and smoothed by capacitor $C_1$ into a D.C. output. The current from the D.C. circuit flows through resistor $R_1$ and the collector and emitter of transistor $TR_1$. From there current flows through the parallel connection of base protecting resistor $R_2$ and diode $D_7$.

Figure 2:
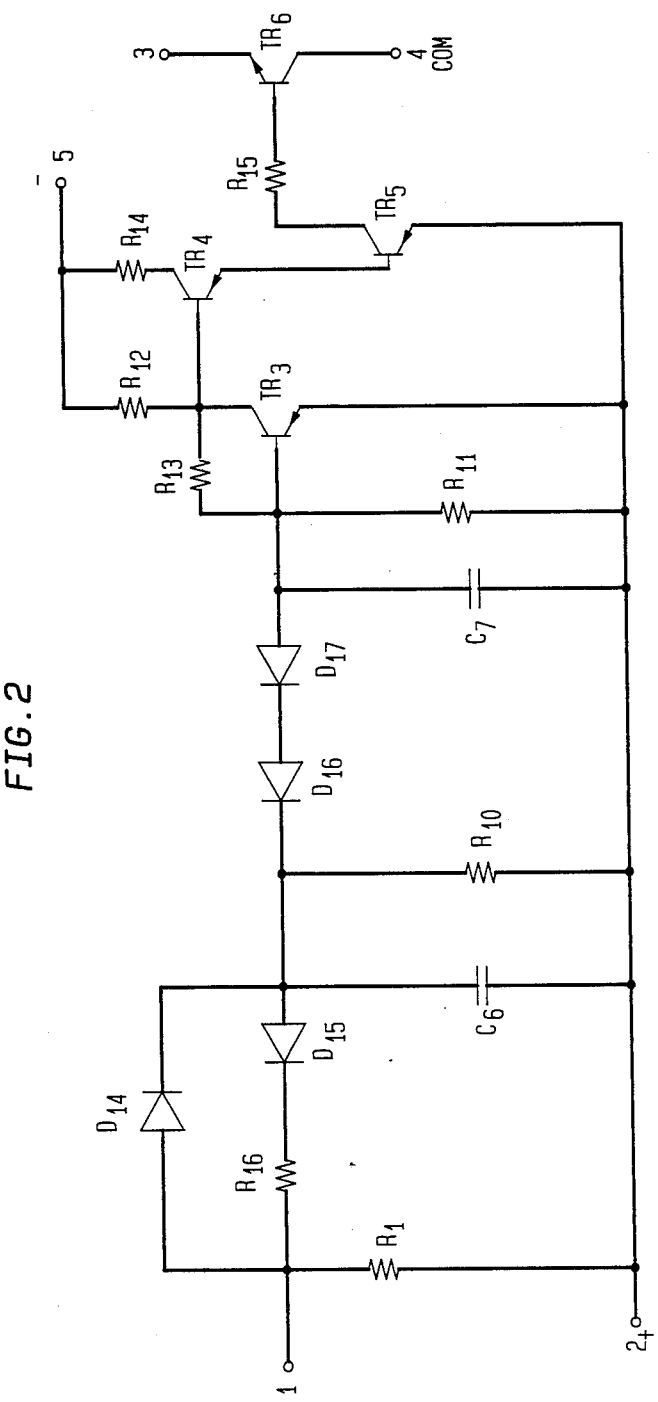
FIG. 2 is a circuit diagram of the safety circuit which protects the three terminal regulating IC.

Power to the motor M is regulated by a three terminal regulating circuit IC. Resistor $R_3$ controls the amount of feedback from the motor M. Selective switches $R_5$ and $R_6$ control the amount of feedback. A double pole single throw alternating switch SW controls which resistor $R_5$ or $R_6$ is chosen. The output terminal of the three terminal regulating circuit IC is connected to the base of transistor $TR_1$ and to the amplifier control diode $D_8$ and through resistor $R_4$ to the base of transistor $TR_2$. The emitter of transistor $TR_2$ is connected back to the output terminal of the regulating IC. The collector of transistor $TR_2$ is connected to the common COM terminal of the IC. The collector of transistor $TR_2$ is also connected to an RC time constant control capacitor $C_4$. The safety overload circuit shown in FIG. 2 is connected across terminals 3 and 4 during normal operation. The RC control capacitor $C_4$ is connected through resistor $R_7$ to diode $D_{10}$ and variable resistor $VR_1$ which controls the variable speed of motor M. Resistor $R_7$ is also connected to diode $D_{11}$ which is attached to the foot pedal switch of the variable resistor $VR_2$ and through resistor $R_9$ to the negative voltage D.C. source through diode $D_6$, capacitor $C_3$ and resistor $R_8$. The plus and minus outputs of the smooth D.C. source connect to a filter capacitor $C_5$ and blocking diode $D_{12}$ which are connected in parallel. The minus output terminal is connected to Zener diode $D_{13}$ and to variable resistor $VR_1$ in series with Zener diode $D_{13}$, resistor $R_8$ and diode $D_6$ which in turn connect the diode $D_5$ and capacitor $C_2$ which connect to diode $D_2$ and diode $D_4$.

As shown in FIG. 1 the D.C. current of the motor M includes a first D.C. path which flows through resistor $R_1$ transistor $TR_1$ and the base current resistor $R_2$. A second D.C. current path flows through the three terminal regulating IC and resistor $R_3$. The purpose of diode $D_7$ of the first D.C. current path is to bias resistor $R_2$ and prevent an overcurrent situation.

According to the circuit diagram of FIG. 1, an increase of current on the motor M causes a voltage increase across resistor $R_3$. This causes increased base current to transistor $TR_2$. The increased current flows through resistor $R_5$ or $R_6$ as selected by switch SW. The base current to transistor $TR_2$ increases the amount of the current to the common COM terminal of the regulating IC causing capacitor $C_4$ to charge. The increased feedback current to the COM terminal of the IC increases the current to the motor and accelerates the motor speed.

As the motor load increases, the motor current increases through the resistor $R_3$. The voltage increase across $R_3$ increases due to the increased actuating current to transistor $TR_2$ which controls the feedback current in accordance with the RC time constant of $C_4$ and $R_5$ or $C_4$ and $R_6$. The control of the capacitance discharge or capacitor $C_4$ by adjusting the manual variable resistor $VR_1$ through resistor $R_7$ and diode $D_{10}$ enables the setting of the speed of the motor M. And the control of the capacitance discharge of capacitor $C_4$ by adjusting the footsteps variable resisting $VR_2$ through diode $D_{11}$ and resistor $R_9$ causes an increase of the voltage to the common COM terminal of the IC which accordingly increases the output voltage of the IC.

In the meantime, the minus voltage rectifying circuit including capacitors $C_2$ and $C_3$ and diodes $D_5$ and $D_6$ are able to keep the capacitor $C_4$ voltage to zero so that the motor torque can be controlled at its lower speed range.

The amplification of transistor $TR_2$ is controlled by diode $D_8$ and the resistor $R_4$ connected between the emitter and the base of the transistor $TR_2$.

If a short should occur on the motor side of the circuit, damage to the IC is prevented by diode $D_9$ which is connected between the IC and the motor M and causes the capacitor $C_4$ to discharge its charge to the motor side instead of into the IC.

In order to protect the three terminal regulating IC from damage due to motor overcurrent or a motor short, an overload protecting safety circuit, as shown in FIG. 2 is connected between terminals 3 and 4. The safety switching circuit consists of transistors $TR_3$, $TR_4$, $TR_5$ and $TR_6$ which are connected between the common COM terminal of the IC and the capacitor $C_4$. This also places the safety circuit of FIG. 2 in connection with the collector of transistor $TR_2$. The safety circuit of FIG. 2 limits the overcurrent provided to the COM terminal of the IC by switching the path between terminals 3 and 4 on or off in response to the sensing of the voltage difference across both ends of resistor $R_1$.

As shown in FIG. 2, the terminal 1 connected between resistor $R_1$ and the transistor $TR_1$ is connected, in sequence, with the resistance $R_{16}$ diode $D_{15}$, diode $D_{16}$, diode $D_{17}$ and the base terminal of transistor $TR_3$ in series. Between diode $D_{15}$ and diode $D_{16}$, a second R.C. time circuit is formed by capacitance $C_6$ and resistor $R_{10}$ and also between the diode $D_{17}$ and the base terminal of transistor $TR_3$, a third R.C. time constant circuit is comprised of capacitor $C_7$ and resistor $R_{11}$. The collector of transistor $TR_3$ is connected to the base of transistor $TR_4$ which forms a switching circuit with transistors $TR_5$ and $TR_6$.

Resistor $R_{13}$ is connected to a point between the collector of transistor $TR_4$ and the base of $TR_3$. The collector of $TR_6$ is connected to the COM terminal of the IC and the emitter of the $TR_6$ is connected to a point between the capacitor $C_4$ and the collector of transistor $TR_2$.

As also shown in FIG. 2, the terminal 2 is connected to the power source and terminal 5 is connected to ground or earth. Diode $D_{14}$ permits the capacitor $C_6$ to be a temporary power source if the original power source suddenly cuts off. Resistor $R_{12}$ is connected to the base of transistor $TR_4$. Resistors $R_{14}$ and $R_{15}$ are respectively connected to the collectors of transistors $TR_4$ and $TR_5$.

The current from resistor $R_{12}$ actuates the switching circuit which comprises transistors $TR_4$, $TR_5$ and $TR_6$. Current from resistors $R_{12}$ normally turns the three transistors "ON" in the normal condition, this is the case because transistor $TR_3$ is normally in the "OFF" state because the voltage caused by the feedback resistors $R_{11}$ and $R_{13}$ do not provide sufficient bias to turn the transistor $TR_3$ on.

However, if any overload should occur on the motor M or a surge of current suddenly is drawn through the motor M as in the case of a short, an increased potential difference will arise across both terminals of the resistor $R_1$. The increased potential difference causes the capacitors $C_6$ and $C_7$ to discharge through resistors $R_{10}$ and $R_{11}$ according to their respective RC time constant. The current discharged by the capacitors $C_6$ and $C_7$ actuates the transistor $TR_3$ which had been in the "OFF" state. Transistor $TR_3$ then begins to conduct, i.e., thus turns "ON" and current from resistor $R_{12}$ flows through the collector the emitter of transistor $TR_3$. The conduction of transistor $TR_3$ shunts the current through resistor $R_{12}$ thereby robbing transistor $TR_4$ of its exitation. Transistor $TR_4$ then turns "OFF" which, in sequence, cause transistors $TR_5$ and $TR_6$ to turn off. Turning off transistor $TR_6$ cuts off the current to the COM terminal of the three terminal regulating IC. This causes an open circuit between $C_4$ and the COM terminal of the IC thereby preventing electrical damage to the IC.

In view of the foregoing, it is clear that the invention comprises a D.C. motor control circuit for adjusting the torque of a D.C. motor at a constant speed. In addition, the invention comprehends a means for preventing damage to the regulating integrated circuit IC if there should be a motor overload or short condition.

The invention has been described with reference to the preferred embodiment thereof it will be appreciated by those of those of ordinary skill in the art that various changes can be made to the parts and the circuit just described without departing from the spirit and scope of the invention as a whole.

We claim:

1. An adjustable torque D.C. motor control circuit apparatus for controlling the torque of small medical motors at a constant speed, said apparatus comprising:
    a source of positive and negative D.C. potential;
    a three terminal regulating circuit connected to said source of D.C. potential and having one input connected to said D.C. source, an output connected to said motor and a common terminal;
    a first capacitor and resistor means connected between said common terminal and said source of D.C. potential;
    feedback means connected between said motor and said first capacitor and resistor means for sensing the increased current load on said motor and for increasing the voltage to said common terminal of said three terminal regulating circuit to increase the output voltage of said IC circuit;
    first variable resistor means connected to said first capacitor and resistor means for controlling the discharge of said first capacitor and resistor means and thereby controlling the speed of said motor;
    a second variable resistor means also connected to said first resistor and capacitor means for controlling the speed of said motor, said second variable resistor means comprising a foot step control of variable resistor;
    IC protection means connected between said first capacitor and resistor means and the common terminal of said IC circuit for protecting said IC circuit from a sudden surge of current if an overload occurs on said motor;
    a load resistor $R_1$ connected across the input and output terminals of said IC regulating circuit;
    a second capacitor and resistance means connected across said load resistance $R_1$;
    transistor switch means connected to said second capacitor and resistance means, the output of said transistor switch means being connected between said common terminal of said IC circuit and said first capacitor and resistance means,
    wherein a change of potential across said load resistor $R_1$ above a certain predetermined value will cause said transistor switching means to electrically disconnect the common terminal of said IC regulating circuit to said first capacitor resistance means.

* * * * *